(12) United States Patent
Sachdeva et al.

(10) Patent No.: US 6,431,863 B1
(45) Date of Patent: Aug. 13, 2002

(54) ENDODONTIC INSTRUMENTS HAVING IMPROVED PHYSICAL PROPERTIES

(76) Inventors: Rohit Chaman Lal Sachdeva, 2605 Courtside La., Plano, TX (US) 75093; Farrokh Farzin-Nia, 141 W. Fairview Blvd., Inglewood, CA (US) 90302

( * ) Notice: Subject to any disclaimer, the term of this patent is extended or adjusted under 35 U.S.C. 154(b) by 1017 days.

(21) Appl. No.: 08/942,732

(22) Filed: Oct. 2, 1997

Related U.S. Application Data

(63) Continuation of application No. 08/453,969, filed on May 30, 1995, now abandoned.

(51) Int. Cl.[7] ................................................ A61C 5/02
(52) U.S. Cl. ...................................... 433/102; 433/224
(58) Field of Search ................................. 433/102, 224

(56) References Cited

U.S. PATENT DOCUMENTS

| | | | |
|---|---|---|---|
| 4,182,040 A | | 1/1980 | Bechtold, Jr. |
| 4,600,391 A | | 7/1986 | Jacob |
| 4,836,780 A | | 6/1989 | Buchanan |
| 4,971,556 A | | 11/1990 | Ritano |
| 4,990,088 A | * | 2/1991 | Weissman .................... 433/102 |
| 5,066,230 A | | 11/1991 | Weissman |
| 5,125,838 A | | 6/1992 | Seigneurin |
| 5,389,226 A | * | 2/1995 | Scruggs et al. ................ 205/50 |
| 5,464,362 A | * | 11/1995 | Heath et al. ................. 433/102 |

OTHER PUBLICATIONS

H. Walia et al., "An Initial Investigation of the Bending and Torsional Properties of Nitinol Root Canal Files", Journal of Endodontics, vol. 14, No. 7, Jul. 1988, pp. 346–351.
Croopnick, G.A. et al., "A Low Environmental–Risk Replacement for Chromium and Electroless Nickel", Metal Finishing, pp. 13–16 (Apr. 1994).
The Kerr Endo Difference Brochure, Kerr Manufacturing Company, Romulus, Michigan 1991.

* cited by examiner

Primary Examiner—Ren Yan
(74) Attorney, Agent, or Firm—Wood, Herron & Evans, L.L.P.

(57) ABSTRACT

Endodontic instruments, including files, reamers, and broaches, wherein the working shaft portion has flexibility/stiffness properties and hardness properties that may vary along its length. These variations in physical properties can be accomplished by utilization of specific materials having a prescribed amorphous phase content, by application of specific coatings or surface treatments, or by selective or differential heat treatment.

3 Claims, 2 Drawing Sheets

ENDODONTIC INSTRUMENTS HAVING IMPROVED PHYSICAL PROPERTIES

RELATED APPLICATION

This application is a continuation of application Ser. No. 08/453.969 filed on May 30, 1995, entitled ENDODONTIC INSTRUMENTS HAVING IMPROVED PHYSICAL PROPERTIES now abandoned.

FIELD OF THE INVENTION

The invention relates to endodontic instruments, and more particularly to such instruments having improved physical properties in the nature of combined flexibility and hardness.

BACKGROUND OF THE INVENTION

Endodontic instruments, particularly files, reamers and broaches, are used for both cleaning and shaping root canals during endodontic procedures. There are a variety of factors which dictate the required physical characteristics of such instruments. These include the desired stiffness and/or flexibility of the instrument, as well as the sharpness of its cutting edges (which relates to the hardness as well as the structure of the material) coupled with certain dimensional and design limitations for the different root canals.

In the past, endodontic instruments have been made from carbon steels and stainless steels due to the propensity of these materials for maintaining adequate cutting edges, as well as the relatively high stiffness thereof. For example, carbon steel and stainless steel endodontic instruments are available from Kerr Corporation, Romulus, Michigan. Endodontic instruments constructed of such materials have certain drawbacks, however, including flexibility limitations which do not allow the instrument to readily conform to the shape of a curved root canal. This inflexibility can cause excessive, unwanted erosion of the root canal.

Recently, there have been some attempts in the endodontic instrument field to address these problems. More particularly, titanium based alloys and Ni/Ti materials have been introduced for use in the manufacture of endodontic instruments. For example, Seigneurin U.S. Pat. No. 5,125,838 relates to endodontic canal instruments made of titanium or titanium alloys. The use of materials such as titanium or Ni/Ti have certain advantages in the flexibility of the material. However, endodontic instruments of such materials may have as a drawback the lack of necessary stiffness, particularly in small sized (diameter) instruments, sufficient to provide guidance in the root canals. Furthermore, the sharpness of the cutting edges in such instruments is compromised due to the lower hardness of the material.

What is needed is an instrument which combines the desired stiffness and sharp edge-maintaining characteristics along with desired enhanced flexibility so as to alleviate canal erosion.

SUMMARY OF THE INVENTION

In its broadest aspects, the present invention is directed to endodontic instruments which include a working shaft portion wherein the shaft portion has a modulus of elasticity that provides enhanced flexibility along its length and yet is stiff enough to provide the necessary guidance for the instrument. Furthermore, the working shaft has sufficient hardness so the cutting edges maintain their sharpness. The shaft may have varying flexibility and hardness properties along its length; however, the variation in flexibility (modulus) is not to be due solely to any variation in dimensions of the working shaft; e.g., the variation in flexibility is not due solely to a greater diameter at one location relative to another location on the working shaft.

In one aspect, the invention contemplates that at least the working shaft portion of the endodontic instrument, which may be a file, reamer or broach, or other endodontic instrument, is comprised of a titanium-based alloy, or other alloy possessing desirable physical characteristics. Suitable alloys contemplated are Ni—Ti based alloys; Ni—Ti alloys that include Nb or Fe as an additional alloying element; and alloys selected from the group consisting of Ti, Zr, Mo, Co, and Cr-based alloys. All of the above are suitable materials for the endodontic instruments of the present invention so long as the alloy is at least partially amorphous. Preferably, the alloy is structurally greater than about 10% amorphous. By selecting and utilizing an appropriate partially amorphous alloy from the noted group, the endodontic instrument is provided with the desired flexibility/stiffness and hardness properties for the particular endodontic procedure.

In an alternative aspect of the invention, the desired flexibility/stiffness and hardness properties are achieved by providing a coating or surface treatment on at least a portion of an exposed surface of the working shaft. The shaft itself may be a titanium-based alloy, or one of the other types of alloys noted above, and the coating or surface treatment may be continuous or discontinuous over the working shaft. Variations in flexibility and hardness along the length of the working shaft can be achieved utilizing discontinuous or intermittent coatings/surface treatments, or by variations in coating thickness. By utilizing continuous coatings of amorphous materials, such as Amplate, available from ATI of Laguna Niguel, Calif., the stiffness of the tip is improved while minimizing erosion of the cutting edges. Discontinuous TiN or TiAlN coatings can improve the hardness at the cutting edges while selectively increasing the stiffness of the instrument along its length.

In yet another aspect of the invention, the desired flexibility/stiffness and hardness properties can be achieved by selective or preferential heat treatment of the working shaft. Particularly in the embodiment wherein the working shaft portion is comprised of Ni—Ti alloy, selective heat treatment can be used to achieve the desired physical properties. Additionally, adjustments to the proportions of Ni and Ti as well as to the cold work ratio, can be advantageously used to achieve desired physical properties.

Utilizing any one of the above techniques, the flexibility and hardness of the working shaft portion can be varied along the length thereof, or specific hardness and/or flexibility properties can be imparted at specific locations along its length. For example, it is generally desired to have a stiffer tip in an endodontic instrument so as to provide improved cutting ability at the tip and to facilitate directing the instrument into the canal. Whereas the middle section of the working shaft portion of the instrument may need to be less stiff so as to improve steerability of the instrument through the canal, thereby minimizing erosion of the canal walls. This minimizing of canal wall erosion is achieved due to the fact that as the instrument is inserted through the canal, the lower modulus of elasticity of the material at the flexed or bent portion (e.g., the middle section) produces smaller forces against the canal walls, thereby minimizing erosion thereof.

These and other features and advantages of the present invention will become apparent to persons skilled in the art upon review of the detailed description of the invention, taken in conjunction with the drawings.

DETAILED DESCRIPTION OF THE INVENTION

Figure 1:
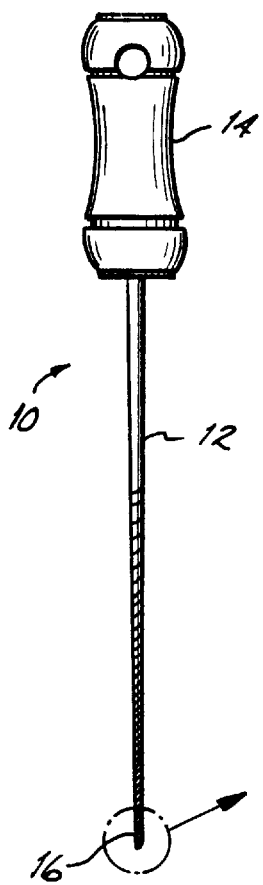
FIG. 1 is a side elevation of an endodontic instrument according to the invention.
Figure 2A:
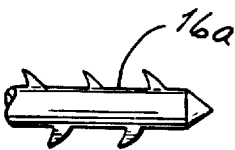
FIGS. 2A–2C are enlarged, partially broken away sections of the area of FIG. 1 encircled at 2.
Figure 2B:
Figure 2C:
Figure 3:
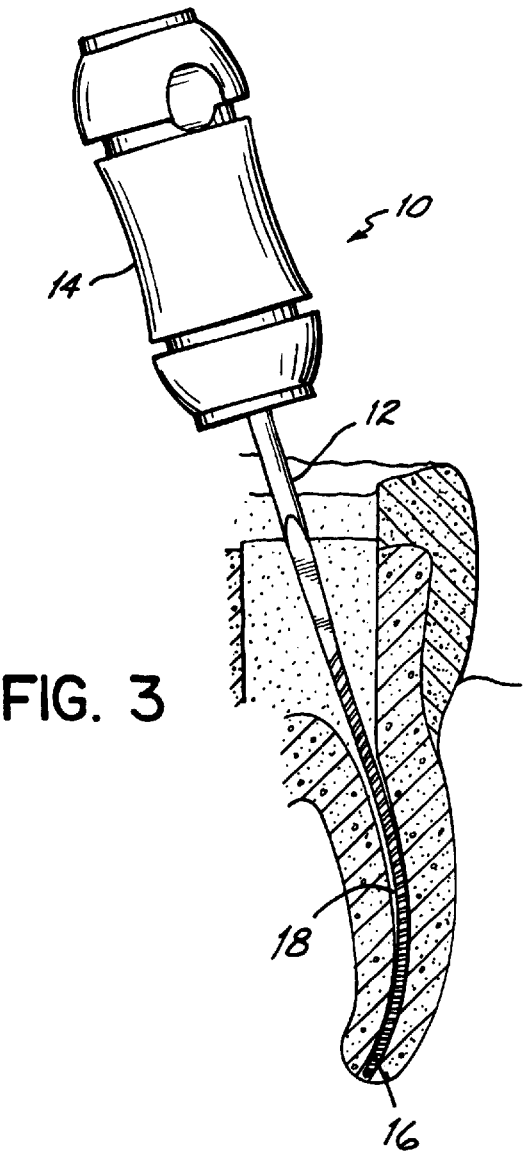
FIG. 3 is an endodontic instrument of FIG. 1 in use.

With reference to the Figures, there is shown in FIG. 1 an endodontic instrument 10 according to the present invention, which includes a working shaft portion 12 and a handle portion 14. FIGS. 2A–2C simply depict enlargements of the tip portion encircled in FIG. 1. More particularly, FIG. 2A shows a barbed broach tip 16a; FIG. 2B shows a typical reamer tip 16b; and FIG. 2C shows a typical file tip 16c. FIG. 3 shows endodontic instrument 10 wherein the working shaft portion 12 has been inserted into a root canal 18 and is flexed to conform to the curvature of the canal.

In a first embodiment, the invention contemplates an endodontic instrument 10 wherein at least the working shaft portion comprises one of the following: (1) a nickel-titanium-based alloy; (2) a nickel-titanium-based alloy including Nb or Fe as an additional alloying element that is present in an amount exceeding about 0.5%, and as much as 1% or more; (3) alloys selected from the group consisting of Ti, Zr, Mo, V, Nb, Co and Cr-based alloys; and (4) other Ti-based alloys which include 10–15% of one or more of the elements in item (3), and up to 5% Al. The modulus of elasticity of the alloys recited in item (4) is expected to be in the range of about 4–17 million psi. In the case of alloys of the type recited in item (3), the alloy must be at least partially amorphous in structure; preferably greater than about 10% amorphous. More specifically, the desired modulus of elasticity and flexibility of the working shaft portion can elasticity and flexibility of the working shaft portion can be achieved by controlling the relative proportion of amorphous structure in the alloy. It is also contemplated that different portions of the working shaft may have different flexibility/stiffness properties and this may be controlled by adjusting the amorphous content of the alloy to different levels at different locations in the working shaft portion 12. That is, the tip 16 may have less amorphous structure than the mid-portion of the working shaft. In that case, the tip would exhibit greater stiffness and hardness than the mid-portion of the working shaft 12.

In an alternative embodiment, the flexibility/stiffness and hardness properties which are desired are achieved by providing a coating or surface treatment, as described below, on at least a portion of an exposed surface of the working shaft. Preferably, the working shaft is a titanium-based alloy. In one specific embodiment, the metal substrate of the working shaft is coated with a continuous metallic layer that is at least partially amorphous. The coating may be applied by an electroplating process such as described in an article by G. A. Croopnick et al. entitled "A Low Environmental-Risk Replacement For Chromium And Electroless Nickel", *Metal Finishing*, pps. 13–16, April, 1994, which is incorporated herein by reference in its entirety. Other processes by which, for example, Ni—W composition can be plated on substrates while forming an amorphous structure, are described in U.S. Pat. No. 5,389,226, the entirety of which is incorporated herein by reference.

Alternatively, the working shaft may be coated with a ceramic material such as TiN, TiC, $Al_2O_3$, $TiO_2$, and other known ceramics. Selection of the coating material and its application will control the ultimate flexibility of the working shaft, as well as its hardness. Additional means for achieving the desired flexibility/stiffness and hardness properties include other coating techniques such as plating, sputtering, plasma deposition, and surface treatment techniques including ion beam implantation, and any other method which allows accurate control of the thickness and/or location of the coating. One specific example is the implantation of nitrogen ions to achieve the desired variation in flexibility of the working shaft. It will be appreciated that discontinuous coatings may serve to appropriately modify the flexibility/stiffness and/or hardness of the working portion at the desired location.

In yet another alternative, the flexibility/stiffness of the instrument can be controlled by selected heat treatment of specific areas of the working shaft. For example, heat treating the working shaft tip 16 at a higher temperature than the treatment temperature of the mid-section will result in greater hardness and stiffness at the tip of the instrument vis-a-vis the mid-section.

Figure 4:
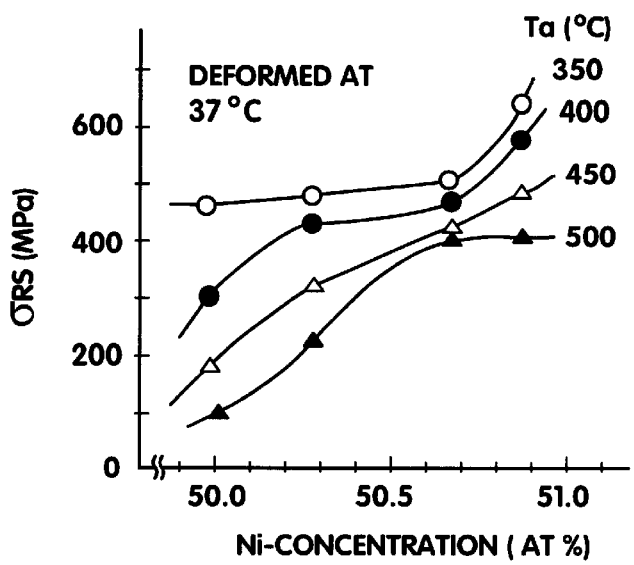
FIG. 4 is a graphical representation of the variation in critical stress for inducing martensite ($\sigma_{MS}$) as a function of Ni concentration.
Figure 5:
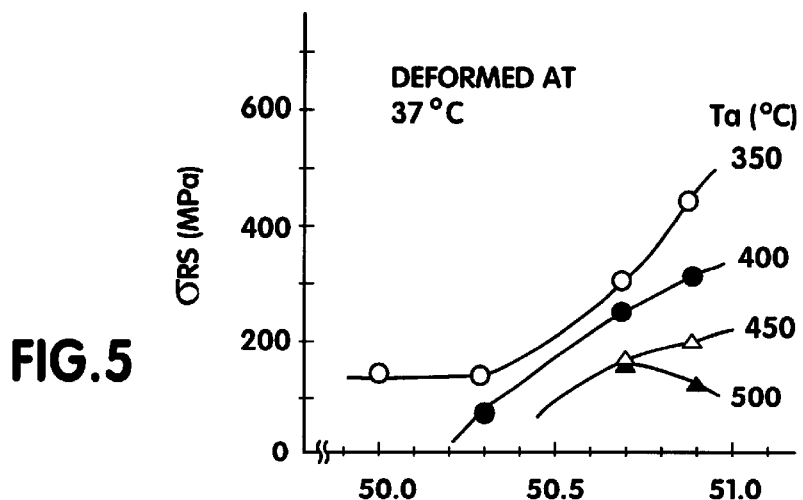
FIG. 5 is a graphical representation of the variation in critical stress for reverse transformation ($\sigma_{RS}$) as a function of Ni concentration.

More particularly, in accordance with the present invention, it is believed that the desired flexibility/stiffness and hardness properties, as discussed below, can be achieved by adjusting the composition of the alloy material, by performing selective heat treatments of the working shaft portion, or by changing the cold work ratio, or any combination of the above. As shown in Table 1 below, and reflected generally in FIGS. 4 and 5, adjusting the Ni content in a Ni—Ti alloy and adjusting the anneal temperature ($T_a$) of that alloy will change the critical stress for inducing martensite ($\sigma_{MS}$) (see FIG. 4), and the critical stress for reverse transformation ($\sigma_{RS}$) (see FIG. 5). All data are for a NiTi wire of 0.018" diameter, having the noted composition and annealed at the noted temperature. Also, the stress values in Table 1 were obtained upon deformation at 25° C., whereas the stress values shown in FIGS. 4 and 5 were obtained upon deformation at 37° C.

TABLE 1

| Annealed at 400° C., deformed at 25° C. | | |
|---|---|---|
| NiTi Alloy Ni % | $\sigma_{MS}$ Martensite | $\sigma_{RS}$ Reverse Transformation |
| 50.9 | 500 MPA | 200 MPA |
| 50.7 | 400 MPA | 100 MPA |
| 50.3 | 325 MPA | 75 MPA |
| 50.0 | 200 MPA | 50 MPA |

Figure 6:
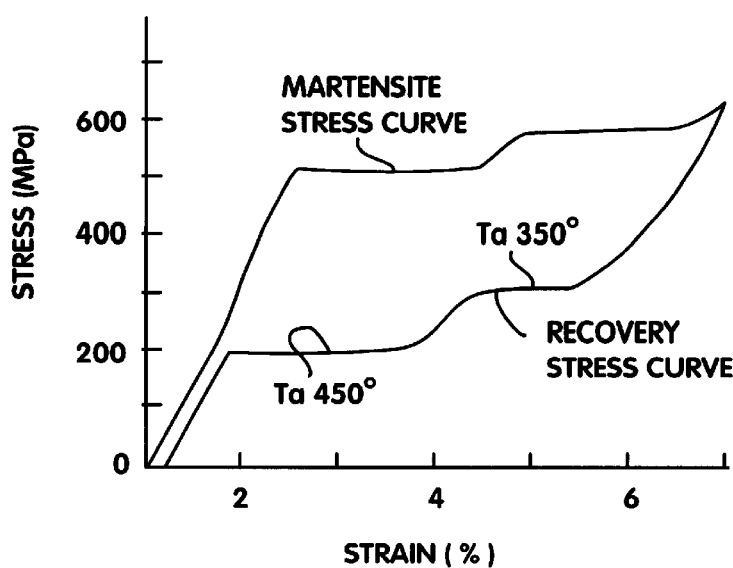
FIG. 6 is a stress-strain curve that shows the effects of differential heat treatment.

FIG. 6 represents, in a graphic manner, the effect of selective heat treatment. The FIG. 6 data is for a Ni—Ti wire (50.6% Ni) of 0.018" diameter wherein a first section was heat treated (annealed) at 450° C., and a second portion was heat treated at 350° C. The variation in stress plateaus for inducing martensite and for reverse transformation are apparent at the noted anneal temperatures. Thus it will be appreciated by persons skilled in the art that variable heat treatments of the working shaft portion 12 of the endodontic instruments of the present invention can be advantageously utilized to achieve the desired properties.

Generally speaking, it is desired that the endodontic instruments according to the present invention have a hardness in the range of 20–60 $R_c$ (Rockwell hardness scale) and flexibility/stiffness (as represented by the modulus of elasticity) in the range of 4 million to 17 million psi.

Having now described the invention with respect to specific features and embodiments, persons having ordinary skill in the art will readily ascertain that various changes and modifications may be made without departing from the scope of the invention, as defined in the appended claims.

What is claimed is:

1. An endodontic instrument including a working shaft portion wherein said working shaft portion has varying stiffness/flexibility properties along at least a portion of its length, said variation in stiffness/flexibility not being due solely to any variation in dimensions or cross-sectional shape of said working shaft, further comprising a coating on at least a portion of an exposed surface of said working shaft portion, said coating resulting in said variation in stiffness/flexibility, and wherein said coating has a thickness gradient along the length of said working shaft portion.

2. An endodontic instrument including a working shaft portion wherein said working shaft portion has varying stiffness/flexibility properties along at least a portion of its length, said variation in stiffness/flexibility not being due solely to any variation in dimensions or cross-sectional shape of said working shaft wherein said variation in stiffness/flexibility is due to selective heat treatment of portions of said working shaft portion.

3. An endodontic instrument including a working shaft portion comprising a NiTi-based alloy, said working shaft portion having stiffness/flexibility properties that vary along at least a portion of its length, said variation in stiffness/flexibility not being due solely to any variation in dimensions or cross-sectional shape of said working shaft, wherein said alloy further includes Nb or Fe in an amount exceeding about 0.5%, and wherein said variation in stiffness/flexibility is due to selective heat treatment of portions of said working shaft.

* * * * *